United States Patent [19]

Iwasaki

[11] Patent Number: 5,032,730
[45] Date of Patent: Jul. 16, 1991

[54] IMMUNOASSAY APPARATUS

[75] Inventor: Osamu Iwasaki, Kanagawa, Japan

[73] Assignee: Fuji Photo Film Co., Ltd., Kanagawa, Japan

[21] Appl. No.: 591,181

[22] Filed: Oct. 1, 1990

[30] Foreign Application Priority Data

Oct. 2, 1989 [JP] Japan ................................. 1-257423
Oct. 3, 1989 [JP] Japan ................................. 1-258536

[51] Int. Cl.$^5$ ...................... G01J 5/00; G01N 33/53; G01N 33/533
[52] U.S. Cl. ........................... 250/461.2; 250/458.1; 436/172
[58] Field of Search ............... 250/458.1, 461.1, 461.2; 422/82.07, 82.08, 93; 436/172

[56] References Cited

U.S. PATENT DOCUMENTS

| 4,133,873 | 1/1979 | Noller | 250/461.2 X |
| 4,222,743 | 9/1980 | Wang | 250/458.1 X |
| 4,279,506 | 7/1981 | Maines | 250/458.1 X |
| 4,447,546 | 5/1984 | Hirschfeld | 250/461.2 X |
| 4,498,782 | 2/1985 | Proctor et al. | 356/440 X |
| 4,931,384 | 6/1990 | Layton et al. | 435/7 |
| 4,980,278 | 12/1990 | Yamada et al. | 435/7 |

OTHER PUBLICATIONS

Flore, M. et al., "The Abbott IMx Automated Benchtop Immunochemistry Analyzer System", Clinical Chemistry, vol. 34, No. 9, (1988), pp. 1726-1732.

Primary Examiner—Constantine Hannaher
Assistant Examiner—Jacob M. Eisenberg
Attorney, Agent, or Firm—Sughrue, Mion, Zinn, Macpeak & Seas

[57] ABSTRACT

In an immunoassay apparatus, a washing liquid containing a substrate is applied to a labeled antigen or a labeled antibody. The fluorescent substance formed from the substrate is exposed to stimulating rays, which cause it to produce the fluorescene, and the amount of the fluorescence is measured, whereby the amount of a specific antigen or a specific antibody in a liquid sample carried on a support is determined. A stimulating ray irradiating device guides stimulating rays from a stimulating ray source to the support. A first photodetector monitors the amount of the stimulating rays, and a monitor optical device guides part of the stimulating rays thereto. A second photodetector detects the amount of fluorescence produced by the fluorescent substance, and a fluorescence receiving device guides the fluorescence from the support to the second photodetector. The amount of the fluorescence detected by the second photodetector is normalized with the amount of the stimulating rays detected by the first photodetector. The first and second photodetectors have approximately identical temperature-photodetection sensitivity characteristics.

5 Claims, 3 Drawing Sheets

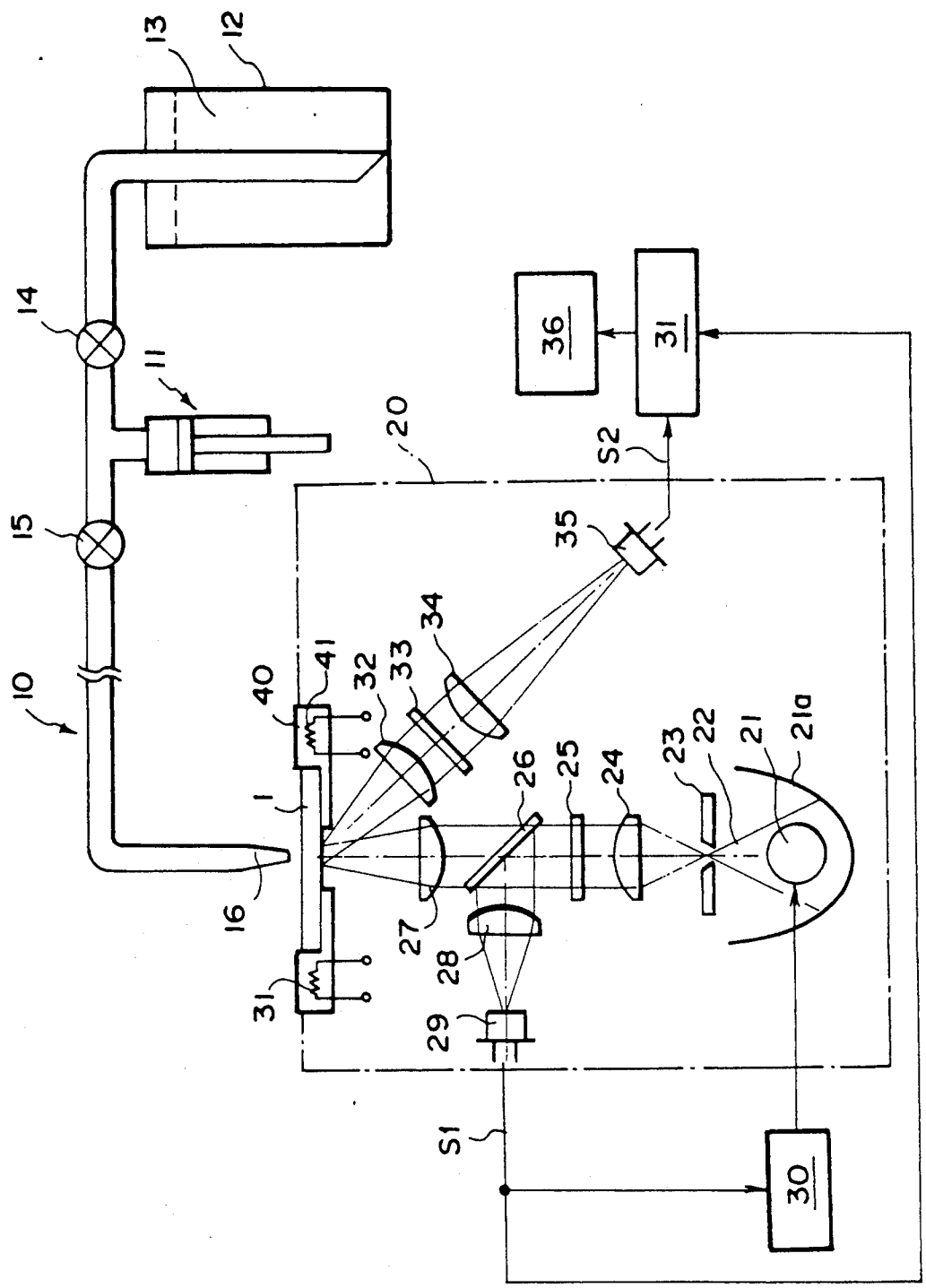

IMMUNOASSAY APPARATUS

BACKGROUND OF THE INVENTION

1. Field of the Invention

This invention relates to an immunoassay apparatus wherein an antigen-antibody reaction is utilized during the determination of the amount of a specific antigen or a specific antibody contained in a liquid sample, such as blood.

2. Description of the Prior Art

Various immunoassay methods, wherein antigen-antibody reactions are utilized during quantitative determinations of biochemical substances, have heretofore been put into practice. The immunoassay methods can be roughly classified into immunodiffusion methods and labeled immunoassay methods. With the immunodiffusion methods, insoluble complexes formed from antigen-antibody reactions are allowed to sediment in gels and the amounts of the insoluble complexes are determined. A typical one of the immunodiffusion methods is the laser nephelometry utilizing the scattering of a laser beam. With the labeled immunoassay methods, antigens or antibodies are labeled such that their amounts can be determined at sensitivities higher than the sensitivities which can be obtained with the immunodiffusion methods. Radioactive isotopes, bacteriophases, enzymes, fluorescent substances, and metals are employed as the labels.

As one of the labeled immunoassay methods wherein enzymes are employed as the labels, a stepwise reaction method has been proposed. With the stepwise reaction method, a support is used to which an antibody (or an antigen) capable of reacting with a specific antigen (or a specific antibody) has been fixed. A droplet of a liquid sample, which is expected to contain the specific antigen (or antibody), is applied to the support, and the specific antigen (or antibody) is allowed to react with the antibody (or antigen), which has been fixed to the support. Thereafter, a labeled specific antigen (or a labeled specific antibody) is applied to the support. A washing liquid, which contains a substrate capable of being converted into a fluorescent substance by the catalytic action of the label, is then poured on the support. The labeled specific antigen (or antibody), which has not reacted with the antibody (or the antigen), is washed out by the washing liquid. Also, the substrate is converted into the fluorescent substance by the action of the labeled specific antigen (or antibody), which has reacted with the antibody (or the antigen). The amount of the fluorescent substance thus formed is determined. From the amount of the fluorescent substance thus determined, a judgment is made as to the presence or absence or the amount of the specific antigen (or antibody) in the liquid sample.

Also, a sandwich method has been proposed wherein an antigen contained in a liquid sample is allowed to react with an antibody, which has been fixed to a support, and a labeled antibody capable of reacting with the antigen is then applied to the support. After the antigen and the labeled antibody have reacted with each other, the labeled antibody, which has not reacted with the antigen, is washed out by a washing liquid. Additionally, a competitive method has been proposed wherein a labeled antigen or a labeled antibody is added to a liquid sample, and the resulting mixture is then applied to a support.

As one of substance suitable as the substrate, 4-methylumbelliferphosphoric acid (hereinbelow be referred to as 4-MUP) has heretofore been known. Also, as one of substances suitable as the fluorescent substance, 4-methylumbelliferone (hereinbelow be referred to as 4-MU) has heretofore been known.

The labeled immunoassay methods described above are advantageous over the conventional wet processes in that the support markedly facilitates the processing and many liquid samples can be analyzed sequentially and automatically.

In immunoassay apparatuses based on the aforesaid principle, the amount of the fluorescent substance generated in the manner described above is determined from the operations wherein stimulating rays, which have wavelengths falling within a predetermined wavelength range, are irradiated to the support, on which the fluorescent substance has been generated, the fluorescent substance is thereby stimulated by the stimulating rays, and the amount of fluorescence produced by the fluorescent substance is measured photoelectrically.

In the conventional immunoassay apparatuses, in order for the accuracy, with which the amount of the fluorescence is measured, to be improved, the amount of the stimulating rays irradiated to the support is monitored, and a signal representing the amount of the stimulating rays is fed back to the stimulating ray source, which produces the stimulating rays. The amount of the stimulating rays produced by the stimulating ray source is thereby stabilized. Alternatively, the amount of the stimulating rays thus monitored is taken into consideration when a signal representing the amount of the fluorescence is processed. However, with the conventional immunoassay apparatuses, in order for a required level of measurement accuracy to be obtained, the temperature of the whole fluorescence amount measuring section must be controlled such that the fluctuation of the temperature may be within the range of, for example, $\pm 1.0°$ C. Therefore, the conventional immunoassay apparatuses become large in size and complicated.

Also, it has been proposed in CLINICAL CHEMISTRY, Vol. 34, No. 9, pp. 1726–1732, 1988, that light, which is produced by a mercury-vapor lamp and which has a wavelength of $\lambda = 365$ nm, may be used as the stimulating rays for the stimulation of 4-MU, and the fluorescence produced by 4-MU is passed through an interference filter having a center transmission wavelength of $\lambda = 450$ nm, or the like, and detected.

However, 4-MU and 4-MUP are simultaneously present on the support, and 4-MUP can also produce the fluorescence. Therefore, when the combination of the stimulating rays having a wavelength of $\lambda = 365$ nm with the light receiving filter having a center transmission wavelength of $\lambda = 450$ nm is employed, the problem occurs in that the fluorescence, which is produced by 4-MU and which is to be detected, and the fluorescence, which is produced by 4-MUP and which causes errors to occur in measurement, cannot sufficiently be separated from each other.

SUMMARY OF THE INVENTION

The primary object of the present invention is to provide an immunoassay apparatus, which enables immunoassays to be carried out at a high accuracy and in which the temperature of the whole fluorescence amount measuring section need not be controlled or may be controlled only roughly.

Another object of the present invention is to provide an immunoassay apparatus in which adverse effects from the fluorescence produced by 4-MUP are minimized and the accuracy of immunoassays is thereby kept high.

The present invention provides a first immunoassay apparatus in which a washing liquid is applied to a labeled antigen or a labeled antibody, the washing liquid containing a substrate capable of being converted into a fluorescent substance by the action of the label of the labeled antigen or the labeled antibody, the fluorescent substance is caused to form by the labeled antigen or the labeled antibody and is then exposed to stimulation rays, which cause the fluorescent substance to produce the fluorescence is measured, whereby the amount of the produced fluorescence is measured, whereby the amount of a specific antigen or a specific antibody in a liquid sample carried on a support is determined, wherein the improvement comprises the provision of a fluorescence amount measuring section which is composed of:
(i) a stimulating ray source which produces said stimulating rays,
(ii) a stimulating ray irradiating optical means which guides said stimulating rays from said stimulating ray source to said support,
(iii) a first photodetector for monitoring the amount of said stimulating rays,
(iv) a monitor optical means which guides part of said stimulating rays to said first photodetector,
(v) a second photodetector for detecting the amount of fluorescence, which has been produced by said fluorescent substance,
(vi) a fluorescence receiving optical means which guides said fluorescence from said support to said second photodetector, and
(vii) a normalizing means for normalizing the amount of said fluorescence, which has been detected by said second photodetector, with the amount of said stimulating rays, which has been detected by said first photodetector,
said first photodetector and said second photodetector having approximately identical temperature-photodetection sensitivity characteristics.

With the first immunoassay apparatus in accordance with the present invention, the first photodetector and the second photodetector have approximately identical temperature-photodetection sensitivity characteristics. Therefore, a temperature drift can be minimized as will be described later. Accordingly, accurate immunoassays can be carried out even when the temperature of the whole fluorescence amount measuring section is not controlled or is controlled only roughly.

The present invention also provides a second immunoassay apparatus in which a washing liquid is applied to a labeled antigen or a labeled antibody, the washing liquid containing a substrate capable of being converted into a fluorescent substance by the action of the label of the labeled antigen or the labeled antibody, the fluorescent substance is caused to form by the labeled antigen or the labeled antibody and is then exposed to stimulating rays, which cause the fluorescent substance to produce the fluorescence, and the amount of the produced fluorescence is measured, whereby the amount of a specific antigen or a specific antibody in a liquid sample carried on a support is determined, wherein the improvement comprises:

(i) using 4-methylumbelliferphosphoric acid as said substrate,
(ii) causing 4-methylumbelliferphosphoric acid to be converted into 4-methylumbelliferone, which serves as said fluorescent substance, by the action of said label,
(iii) exposing said support to the stimulating rays having a wavelength distribution such that the center wavelength falls within the range of 370 nm to 375 nm and $\Delta\lambda(1/10)$ is not wider than 5 nm, where $\Delta\lambda(1/10)$ denotes the wavelength range in which the intensity becomes 1/10 of the center intensity of the spectrum, and
(iv) detecting the fluorescence, which has been radiated out of said support, through a filter having a transmission characteristic such that the center transmission wavelength falls within the range of $460\pm5$ nm and $\Delta\lambda(1/10)$ is not wider than 10 nm, whereby the amount of said specific antigen or said specific antibody in said liquid sample is determined.

With the second immunoassay apparatus in accordance with the present invention, the support is exposed to the stimulating rays having a wavelength distribution such that the center wavelength falls within the range of 370 nm to 375 nm and $\Delta\lambda(1/10) \leq 5$ nm. Also, the fluorescence, which has been radiated out of the support, is detected through the filter having a transmission characteristic such that the center transmission wavelength falls within the range of $460\pm5$ nm and $\Delta\lambda(1/10) \leq 10$ nm. Therefore, adverse effects from the fluorescence produced by 4-MUP can be minimized, and the accuracy of immunoassays can be kept high. Additionally, adverse effects from light scattered by the Raman effect can be eliminated.

BRIEF DESCRIPTION OF THE DRAWINGS

FIG. 1 is a schematic view showing an embodiment of the immunoassay apparatus in accordance with the present invention.

DESCRIPTION OF THE PREFERRED EMBODIMENTS

The present invention will hereinbelow be described in further detail with reference to the accompanying drawings.

FIGS. 2A through 2F are explanatory views showing the principle of an immunoassay carried out with an embodiment of the immunoassay apparatus in accordance with the present invention.

Figure 2A:
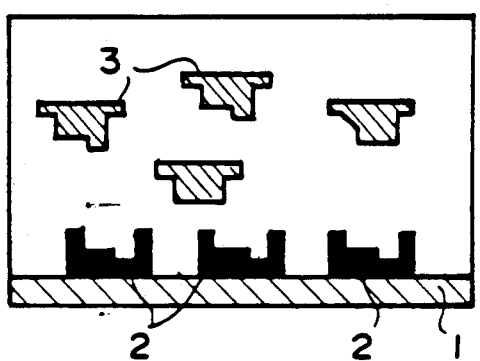
FIGS. 2A through 2F are explanatory views showing the principle of an immunoassay carried out with an embodiment of the immunoassay apparatus in accordance with the present invention.
Figure 2B:
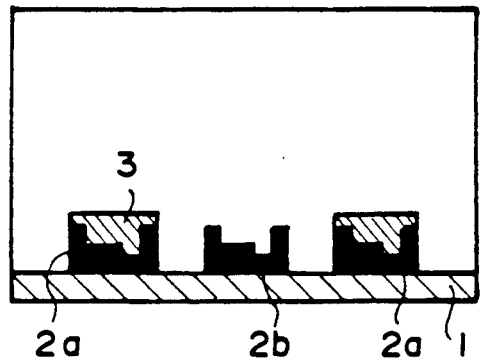

With reference to FIG. 2A, antibodies 2, 2, . . . have been fixed to a slide 1, which serves as a support. (In FIG. 2A, only two antibodies 2, 2 are shown.) A droplet of blood containing antigens 3, 3, . . . is applied to the slide 1. (In FIG. 2A, only a single antigen 3 is shown.) As illustrated in FIG. 2B, depending on the amount of the antigens 3, 3, . . . in the blood, an antibody 2a reacts with an antigen 3, and an antibody 2b remains unreacted. As the amount of the antigens 3, 3, . . . in the blood is larger, more antibodies 2a, 2a, . . . react with the antigens 3, 3, ..., and less antibodies 2b, 2b, ... remain unreacted.

Figure 2C:
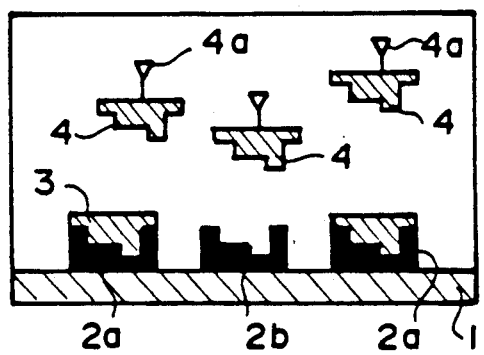
Figure 2D:
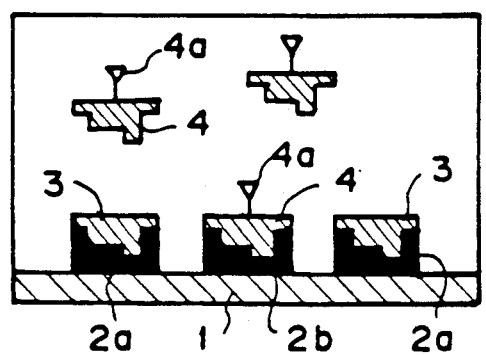

Thereafter, as illustrated in FIG. 2C, antigens 4, 4, ... provided with labels 4a, 4a, ... are applied to the slide 1. (In FIG. 2C, only two labeled antigens 4, 4 are shown.) As shown in FIG. 2D, one of the labeled antigens 4, 4 reacts with the antibody 2, which has not reacted with an antigen 3 contained in the blood. The other labeled antigen 4 remains unreacted.

Figure 2E:
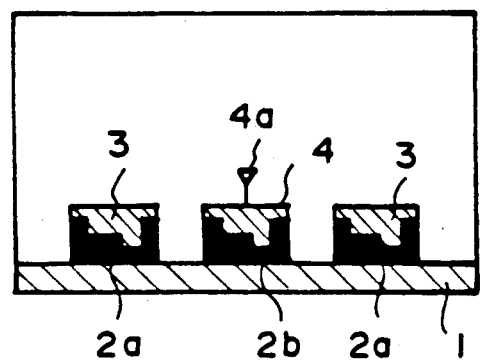
Figure 2F:
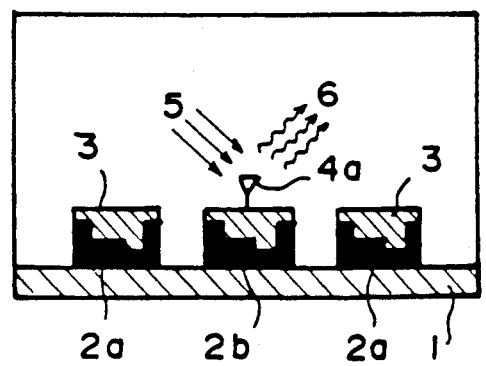

A predetermined amount of a washing liquid, which contains a substrate 5, is then poured on the slide 1 for a period of, for example, 30 seconds. As a result, as illustrated in FIG. 2E, the labeled antigen 4, which has not reacted with the antibody 2, is washed out. Thereafter, as illustrated in FIG. 2F, the substrate 5 is converted into a fluorescent substance 6 by the catalytic action of the label 4a. After the washing liquid has been poured on the slide 1 for 30 seconds, stimulating rays are irradiated to the slide 1 at intervals of, for example, 10 seconds. The intermittent irradiation is carried out for five minutes. When the slide 1 is exposed to the stimulating rays, the fluorescent substance 6 produces the fluorescence. The amounts of the produced fluorescence are measured. From the measured amounts of the fluorescence, a change in the amount of the generated fluorescent substance 6 with the passage of time is found. The change in the amount of the generated fluorescent substance 6 with the passage of time is compared with a predetermined calibration curve, and the amount of the antigens 3, 3, ... contained in the blood is thereby determined.

FIG. 1 is a schematic view showing an embodiment of the immunoassay apparatus in accordance with the present invention, wherein the principle of immunoassay described above is employed. FIG. 1 primarily shows a fluorescence amount measuring section 20.

With reference to FIG. 1, a slide 1 is placed at the upper part of the fluorescence amount measuring section 20. The slide 1 is kept at a predetermined temperature (e.g. 37.5° C.) by a heater 41, which is incorporated in an incubator 40.

Thereafter, blood 13, which is contained in a vessel 12, is taken up by a syringe 11 of a sample application means 10 via a valve 14. The blood 13 passes through a valve 15, and a predetermined amount of the blood 13 is applied from a nozzle 16 to the slide 1. (This operation corresponds to the steps shown in FIGS. 2A and 2B.)

In the same manner as that for the blood 13, a droplet of a liquid, which contains enzyme-labeled antigens, is then applied to the slide 1 by a liquid application means (not shown). The liquid application means may be constituted in the same manner as the sample application means 10. (This operation corresponds to the steps shown in FIGS. 2C and 2D.) Thereafter, a predetermined amount of a washing liquid, which contains a substrate, for example, 4-MUP, is poured on the slide 1 for 30 seconds. (This operation corresponds to the step shown in FIG. 2E.) For this purpose, a liquid application means (not shown) may be employed which is constituted in the same manner as the sample application means 10. After the washing liquid is stopped, the amount of 4-MU, into which 4-MUP has been converted by the enzyme label, is determined at intervals of 10 seconds for a period of five minutes.

In the fluorescence amount measuring section 20, a low-pressure mercury-vapor lamp 21 provided with an ellipsoidal mirror 21a is employed as a stimulating ray source. Stimulating rays 22 are produced by the low-pressure mercury-vapor lamp 21. The stimulating rays 22 pass through a slit of a slit plate 23, a lens 24, an interference filter 25, a plane-parallel plate 26, and a lens 27. The simulating rays 22 then impinge upon the slide 1 from below. The interference filter 25 transmits only the bright line having a wavelength of $\lambda = 365$ nm among the simulating rays 22 produced by the low-pressure mercury-vapor lamp 21. Therefore, 4-MU formed on the slide 1 is exposed to and stimulated by the stimulating rays having a wavelength of $\lambda = 365$ nm.

The stimulating rays, which have been reflected by the plane-parallel plate 26, pass through a lens 28 and is detected by a first photodetector 29. In this manner, the amount of the stimulating rays is monitored. A monitor signal S1 generated by the first photodetector 29 is fed into an electric power source 30 and is used to control the voltage applied to the low-pressure mercury-vapor lamp 21 such that the low-pressure mercury-vapor lamp 21 produces a predetermined amount of the stimulating rays 22. The signal S1 is also fed to a signal processing means 31.

When 4-MU formed on the slide 1 is stimulated by the stimulating rays having a wavelength of $\lambda = 365$ nm, it produces the fluorescence. The fluorescence passes through a lens 32, an interference filter 33, and a lens 34, and is photoelectrically detected by a second photodetector 35. The interference filter 33 transmits only the fluorescence having wavelengths falling within a narrow wavelength range (having a half-width of, for example, 5 nm) around $\lambda = 450$ nm.

The second photodetector 35 generates a signal S2 representing the amount of the fluorescence. The signal S2 is fed into the signal processing means 31. As described above, the signal processing means 31 also receives the signal S1 from the first photodetector 29. The signal processing means 31 normalizes the signal S2 with the signal S1. In this manner, the measurement and calculation are carried out at intervals of 10 seconds for a period of five minutes, and a graph representing the rate, with which 4-MU is formed, is obtained. After the measurements are finished within a total time of five minutes, the amount of the antigens contained in the blood 13 is determined from the graph thus obtained. A value representing the amount of the antigens contained in the blood 13 is displayed on a display device 36.

How the fluorescence amount measuring section 20 depends on temperature will be described hereinbelow.

The amount of the stimulating rays 22, which are produced by the low-pressure mercury-vapor lamp 21, can be expressed as I(T), i.e. a function of temperature, T. The transmittance of the interference filter 26 can be expressed as F1(T), i.e. a function of temperature, T. Also, the transmittance of the interference filter 33 can be expressed as F2(T), i.e. a function of temperature, T. The photodetection sensitivity of the first photodetector 29 can be expressed as S1(T), i.e. a function of temperature, T. Also, the photodetection sensitivity of the second photodetector 35 can be expressed as S2(T), i.e. a function of temperature, T.

The amount, Iex, of the stimulating rays, which impinge upon the slide 1, can be expressed as $$I_{ex} = k_0 \cdot I(T) \cdot F_1(T) \tag{1}$$

where k0 denotes a fixed number. The amount, Iem, of the fluorescence radiated out of the slide 1 is proportional to the amount, Iex, of the stimulating rays impinging upon the slide 1, and can be expressed as $$I_{em} = \eta \cdot I_{ex} = \eta \cdot k_0 \cdot I(T) \cdot F_1(T) \quad (2)$$

Therefore, from Formula (2), the transmittance of the interference filter 33, F2(T), and the photodetection sensitivity of the second photodetector 35, S2(T), the value of the signal S2 generated by the second photodetector 35 is expressed as $$S2 = k_1 \cdot I(T) \cdot F_1(T) \cdot F_2(T) \cdot S_2(T) \quad (3)$$

where k1 denotes a fixed number.

Also, the value of the signal S1 generated by the first photodetector 29 is expressed as $$S1 = k_2 \cdot I(T) \cdot F_1(T) \cdot S_1(T) \quad (4)$$

The signal S2 generated by the second photodetector 35 is normalized with the signal S1 generated by the first photodetector 29. From the normalization, a normalized signal S3 is obtained, which is expressed as $$S3 = S2/S1 = k \cdot F_2(T) \cdot \frac{S_2(T)}{S_1(T)} \quad (5)$$

In cases where the photodetection sensitivity of the first photodetector 29, S1(T), and the photodetection sensitivity of the second photodetector 35, S2(T), are in a proportional relation to each other, i.e. in cases where they change in the same way even through they have dependence on temperature, the value of S2(T)/S1(T) becomes constant. Also, the dependence of the transmittance and the center transmission wavelength of the interference filter 33 on temperature is very low. Additionally, the spectrum of the fluorescence ranges over a wide wavelength width. Therefore, even if the center transmission wavelength of the interference filter 33 changes slightly, the amount of the fluorescence, which passes through the interference filter 33, will not change substantially. Accordingly, the dependence of the signal S3, which is obtained ultimately, on temperature is very low. For this reason, no particular temperature control is required for the fluorescence amount measuring section 20.

Another embodiment of the immunoassay apparatus in accordance with the present invention will be described hereinbelow.

This embodiment is based on the same immunoassay principle as that described above with reference to FIGS. 2A through 2F. As in the embodiment described above, 4-MUP is employed as the substrate 5. The washing liquid containing 4-MUP 5 takes the form of an aqueous solution. As described above, 4-MUP 5 is converted into 4-MU, which serves as the fluorescent substance 6, by the catalytic action of the label 4a.

Figure 3:
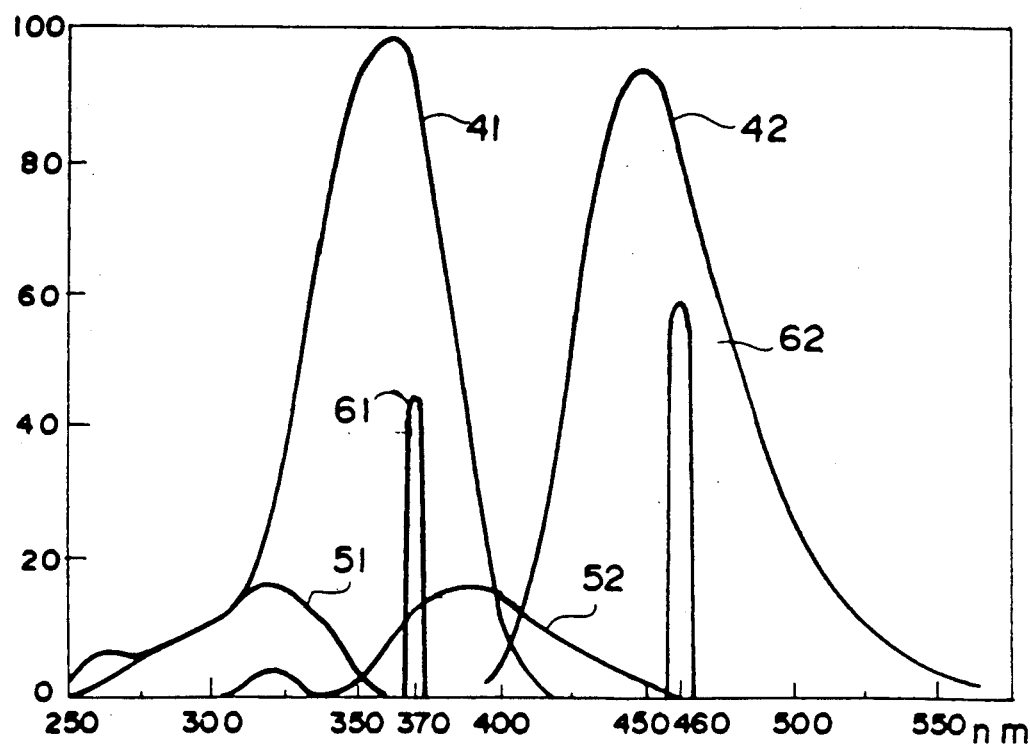
FIG. 3 is a graph showing stimulation spectra and fluorescence spectra of 4-MUP and 4-MU.

FIG. 3 is a graph showing stimulation spectra and fluorescence spectra of 4-MUP and 4-MU.

With reference to FIG. 3, curve 41 indicates the stimulation spectrum of 4-MU, i.e. the spectrum of stimulating rays with which 4-MU can be stimulated. Curve 41 indicates the spectrum of the fluorescence produced by 4-MU. Curves 51 and 52 respectively indicate the stimulation spectrum and the fluorescence spectrum of 4-MUP. As illustrated, 4-MUP also produces the fluorescence. Therefore, when the fluorescence produced by 4-MU is detected, the fluorescence produced by 4-MUP will be undesirably detected together with the fluorescence produced by 4-MU. In such cases, the fluorescence produced by 4-MUP causes an error to occur in immunoassays.

Experiments were carried out wherein 4-MU and 4-MUP were independently stimulated with stimulating rays having various wavelengths, and the amounts of the fluorescence produced thereby were measured. Tables 1 and 2 show the results of the experiments. In these tables, the amounts of the fluorescence produced are shown as relative values. Table 1 is for the cases where the stimulation wavelength width was 5 nm. Table 2 is for the cases where the stimulation wavelength width was 3 nm.

TABLE 1

| Wavelength of stimulating rays (nm) | A: Amount of 4-MU fluorescence (relative value) | B: Amount of 4-MUP fluorescence (relative value) | A/B |
| --- | --- | --- | --- |
| 355 | 26.5 | 17.7 | 15.0 |
| 360 | 27.0 | 9.1 | 29.6 |
| 365 | 26.5 | 3.5 | 75.7 |
| 370 | 24.5 | 1.8 | 136.2 |

(Stimulation wavelength width: 5 nm)

TABLE 2

| Wavelength of stimulating rays (nm) | A: Amount of 4-MU fluorescence (relative value) | B: Amount of 4-MUP fluorescence (relative value) | A/B |
| --- | --- | --- | --- |
| 355 | 25.3 | 17.8 | 14.2 |
| 360 | 26.0 | 8.3 | 31.4 |
| 365 | 25.4 | 2.9 | 87.4 |
| 370 | 23.7 | 1.7 | 139.2 |

(Stimulation wavelength width: 3 nm)

As will be clear from Tables 1 and 2, in both cases where the stimulation wavelength widths are 5 nm and 3 nm, the value of A/B, i.e. the ratio of the amount of the fluorescence produced by 4-MU to the amount of the fluorescence produced by 4-MUP, is the largest when the center wavelength of the stimulating rays is 370 nm.

The adverse effect of the fluorescence produced by 4-MUP can be reduced also on the side of the fluorescence receiving optical means. Specifically, as indicated by curve 52 in FIG. 3, the fluorescence spectrum of 4-MUP extends to a wavelength of approximately 470 nm. Therefore, it is thought that the fluorescence having wavelengths longer than 470 nm be detected. However, in the long wavelength region, the intensity (i.e. the height of the vertical axis) of the fluorescence spectrum of 4-MU decreases. Therefore, only a small amount of the fluorescence can be detected and, as a result, the S/N ratio will decrease. Accordingly, the fluorescence having wavelengths of approximately 460 nm should preferably be detected.

The fluorescence amount measuring section employed in this embodiment will be described hereinbelow with reference to FIG. 1.

In this embodiment, by way of example, a xenon lamp, which produces light having a continuous spectrum, is employed as the lamp 21 in the fluorescence amount measuring section 20. Also, as the interference filter 25, an interference filter is employed which transmits only the components of the stimulating rays 22 produced by the lamp 21, which components have a wavelength distribution as indicated by curve 61 in FIG. 3 (the vertical axis of the graph shown in FIG. 3 indicates the relative value). Specifically, the interference filter 25 transmits only the stimulating rays, which have a wavelength distribution such that the center wavelength $\lambda$ falls within the range of 370 nm to 375 nm and $\Delta\lambda(1/10)$ is not wider than 5 nm, where $\Delta\lambda(1/10)$ denotes the wavelength range in which the intensity becomes 1/10 of the center intensity of the spectrum. Therefore, 4-MU formed on the slide 1 is stimulated with such stimulating rays which have passed through the interference filter 25.

When 4-MU formed on the slide 1 is stimulated by the stimulating rays having a wavelength of $\lambda=370$ nm, it produces the fluorescence. The fluorescence passes through the lens 32, the interference filter 33, and the lens 34, and is photoelectrically detected by the second photodetector 35. The interference filter 33 employed in this embodiment has the transmission wavelength range indicated by curve 62 in FIG. 3. Specifically, the interference filter 33 transmits only the fluorescence having wavelengths falling within a narrow wavelength range ($\Delta\lambda(1/10) \leq 10$ nm) around $\lambda=460$ nm.

In this embodiment, the slide 1 is exposed to the stimulating rays, which have passed through the interference filter 25 having the center transmission wavelength of $\lambda=370$ nm as indicated by curve 61 in FIG. 3. The fluorescence radiated out of the slide 1 is passed through the interference filter 33 having the center transmission wavelength of $\lambda=460$ nm as indicated by curve 62 in FIG. 3. Only the fluorescence, which has passed through the interference filter 33, is detected. Therefore, the fluorescence produced by 4-MUP is substantially filtered out by the interference filter 33, and the amount of the fluorescence produced by 4-MU can be detected accurately.

Figure 4:
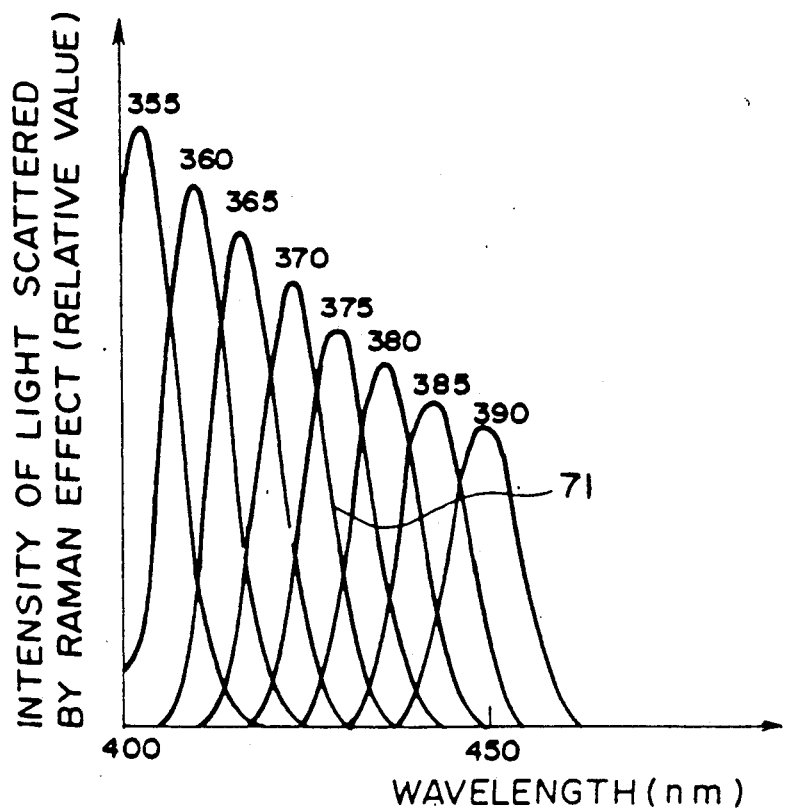
FIG. 4 is a graph showing spectra of light scattered from water by the Raman effect.

FIG. 4 is a graph showing spectra of light scattered from water by the Raman effect. In FIG. 4, numerals indicated above respective curves denote the wavelengths of light irradiated to water. The curves indicate the spectra of light scattered from water by the Raman effect when light having the corresponding wavelengths are irradiated to water.

With the Raman effect, when monochromatic light is irradiated to a substance (the washing liquid or water in this case), scattered light having wavelengths slightly shifted from the wavelengths of the incident light is contained in the light scattered by the substance.

In FIG. 4, curve 71 indicates the spectrum of stimulating rays scattered from the washing liquid (water) by the Raman effect when the stimulating rays having a center wavelength of 370 nm are irradiated to the slide 1. As described above, the interference filter 33 transmits only light having the center wavelength of 460 nm as indicated by curve 62 in FIG. 3. Therefore, the interference filter 33 also filters out the stimulating rays scattered from the washing liquid (water) by the Raman effect. Accordingly, the results of immunoassays are not adversely affected by the stimulating rays scattered from the washing liquid (water) by the Raman effect.

In this embodiment, the center wavelength of the stimulating rays impinging upon the slide 1 is $\lambda=370$ nm. Also, the center wavelength of the fluorescence detected is $\lambda=460$ nm.

In cases where the stimulating ray source, which produces the stimulating rays having a continuous spectrum, and the interference filter are employed, the center wavelength of the transmission spectrum width of the interference filter is limited by the center wavelength $\lambda=365$ nm of the bright line spectrum of the lamp. In this case, consideration may be given to the cases where the center wavelength of the transmission spectrum of the interference filter is $\lambda=370$ nm. Specifically, if the transmission spectrum of the interference filter and the bright line spectrum of the lamp do not overlap each other, the adverse effects of 4-MUP can be made smaller than when the bright line spectrum of the lamp is employed for the stimulation. The width of the bright line spectrum of the lamp is $\Delta\lambda(1/10)=2$ nm to 3 nm. In order that the overlap upon the bright line spectrum be avoided, it is sufficient for the width of the transmission spectrum of the interference filter to be $\Delta\lambda(1/10) \leq 5$ nm.

The width of the transmission spectrum of the interference filter, which is located on the side of the fluorescence receiving optical means, is limited by the Raman spectrum of the washing liquid. In this case, consideration may be given to the cases where the center wavelength of the stimulating rays is $\lambda=375$ nm. As shown in FIG. 4, in cases where the center wavelength of the stimulating rays is 375 nm, the Raman spectrum extends to approximately 445 nm. Therefore, when the center wavelength of the fluorescence detected is the shortest, i.e. $\lambda=455$ nm, it is sufficient for the width of the transmission spectrum of the interference filter, which is located on the side of the fluorescence receiving optical means, to be $\Delta\lambda(1/10) \leq 10$ nm.

In the embodiments described above, the stepwise reaction method is employed. The immunoassay apparatus is also applicable when the sandwich method or the competitive method is employed.

I claim:

1. An immunoassay apparatus in which a washing liquid is applied to a labeled antigen or a labeled antibody, the washing liquid containing a substrate capable of being converted into a fluorescent substance by the action of the label of the labeled antigen or the labeled antibody, the fluorescent substance is caused to form by the labeled antigen or the labeled antibody and is then exposed to stimulating rays, which cause the fluorescent substance to produce the fluorescence, and the amount of the produced fluorescence is measured, whereby the amount of a specific antigen or a specific antibody in a liquid sample carried on a support is determined, wherein the improvement comprises the provision of a fluorescence amount measuring section which is composed of:

(i) a stimulating ray source which produces said stimulating rays, (ii) a stimulating ray irradiating optical means which guides said stimulating rays from said stimulating ray source to said support, (iii) a first photodetector for monitoring the amount of said stimulating rays, (iv) a monitor optical means which guides part of said stimulating rays to said first photodetector, (v) a second photodetector for detecting the amount of fluorescence, which has been produced by said fluorescent substance, (vi) a fluorescence receiving optical means which guides said fluorescence from said support to said second photodetector, and (vii) a normalizing means for normalizing the amount of said fluorescence, which has been detected by said second photodetector, with the amount of said stimulating rays, which has been detected by said first photodetector, said first photodetector and said second photodetector having approximately identical temperature-photodetection sensitivity characteristics.

2. An apparatus as defined in claim 1 wherein said stimulating ray irradiating optical means is provided with a filter which transmits only the stimulating rays having wavelengths falling within a narrow wavelength range.

3. An apparatus as defined in claim 1 wherein said fluorescence receiving optical means is provided with a filter which transmits only the fluorescence having wavelengths falling within a narrow wavelength range.

4. An immunoassay apparatus in which a washing liquid is applied to a labeled antigen or a labeled antibody, the washing liquid containing a substrate capable of being converted into a fluorescent substance by the action of the label of the labeled antigen or the labeled antibody, the fluorescent substance is caused to form by the labeled antigen or the labeled antibody and is then exposed to stimulating rays, which cause the fluorescent substance to produce the fluorescence, and the amount of the produced fluorescence is measured, whereby the amount of a specific antigen or a specific antibody in a liquid sample carried on a support is determined, wherein the improvement comprises:

(i) using 4-methylumbelliferphosphoric acid as said substrate, (ii) causing 4-methylumbelliferphosphoric acid to be converted into 4-methylumbelliferone, which serves as said fluorescent substance, by the action of said label, (iii) exposing said support to the stimulating rays having a wavelength distribution such that the center wavelength falls within the range of 370 nm to 375 nm and $\Delta\lambda(1/10)$ is not wider than 5 nm, where $\Delta\lambda(1/10)$ denotes the wavelength range in which the intensity becomes 1/10 of the center intensity of the spectrum, and (iv) detecting the fluorescence, which has been radiated out of said support, through a filter having a transmission characteristic such that the center transmission wavelength falls within the range of $460\pm5$ nm and $\Delta\lambda(1/10)$ is not wider than 10 nm, whereby the amount of said specific antigen or said specific antibody in said liquid sample is determined.

5. An apparatus as defined in claim 4 wherein said filter is an interference filter.

* * * * *